（12) United States Patent
Bertz et al.

US007785573B2

(10) Patent No.: US 7,785,573 B2
(45) Date of Patent: Aug. 31, 2010

(54) SOLUBILIZING AGENTS FOR ACTIVE OR FUNCTIONAL ORGANIC COMPOUNDS

(75) Inventors: Steven H. Bertz, Morristown, NJ (US); Ilya Makarovsky, Fair Lawn, NJ (US); Donna N. Laura, Nutley, NJ (US)

(73) Assignee: ISP Investments Inc., Wilmington, DE (US)

( * ) Notice: Subject to any disclaimer, the term of this patent is extended or adjusted under 35 U.S.C. 154(b) by 203 days.

(21) Appl. No.: 11/337,857

(22) Filed: Jan. 23, 2006

(65) Prior Publication Data

US 2007/0172437 A1   Jul. 26, 2007

(51) Int. Cl.
*A61K 8/00*   (2006.01)
*A61K 8/18*   (2006.01)
*A61K 8/02*   (2006.01)
*A61K 31/21*   (2006.01)
*A61K 31/26*   (2006.01)
*A61Q 17/04*   (2006.01)
*A01N 25/00*   (2006.01)
*A01N 47/00*   (2006.01)
*C07C 69/74*   (2006.01)

(52) U.S. Cl. .................. 424/59; 424/401; 424/405; 514/515; 560/124

(58) Field of Classification Search ............. 424/59, 424/401, 405; 514/515; 560/124
See application file for complete search history.

(56) References Cited

U.S. PATENT DOCUMENTS

| 5,603,923 | A | * | 2/1997 | Robinson et al. | ............. 424/60 |
| 5,733,535 | A | * | 3/1998 | Hollingshead et al. | ........ 424/65 |
| 6,423,329 | B1 | * | 7/2002 | Sine et al. | .................. 424/405 |
| 6,969,522 | B2 | * | 11/2005 | Bessette | ..................... 424/406 |
| 2005/0009863 | A1 | | 1/2005 | Hofmeister et al. | |
| 2005/0079141 | A1 | | 4/2005 | Zander et al. | |
| 2006/0110415 | A1 | * | 5/2006 | Gupta | ........................ 424/401 |

OTHER PUBLICATIONS

PCT, International Search Report issued regarding International Application No. PCT/US2007/001717 (dated Sep. 11, 2007; published Dec. 21, 2007).
PCT, International Preliminary Report on Patentability issued regarding International Application No. PCT/US2007/001717 (Aug. 7, 2008).

* cited by examiner

*Primary Examiner*—Johann R Richter
*Assistant Examiner*—Luke E Karpinski
(74) *Attorney, Agent, or Firm*—William J. Davis; Thompson Hine LLP

(57) ABSTRACT

An active or functional organic compound is solubilized by an ester of an aryl alcohol, e.g., phenethyl, benzyl or substituted benzyl alcohol, and an alkyl or cycloalkyl carboxylic acid, or by a carbonate of said aryl alcohol and an alkyl or cycloalkyl carbonic acid.

14 Claims, No Drawings

SOLUBILIZING AGENTS FOR ACTIVE OR FUNCTIONAL ORGANIC COMPOUNDS

CROSS-REFERENCE TO RELATED U.S. PATENT APPLICATIONS

This application is related to co-pending U.S. patent application Ser. No. 11/007,744, filed Dec. 8, 2004, which described diaryl esters as solubilizing agents, the entire contents of which is incorporated by reference herein.

BACKGROUND OF THE INVENTION

1. Field of the Invention

This invention relates to compositions containing an active or functional organic compound which requires solubilization, and more particularly, to compositions which are effectively solubilized by addition of an ester of an aryl alcohol, e.g., phenethyl, benzyl or substituted benzyl alcohol, and an alkyl or cycloalkyl carboxylic or carbonic acid.

2. Description of the Prior Art

Many commercial products such as personal care (e.g., sunscreens or UV filters), pharmaceutical, agricultural and industrial compositions, contain active or functional materials which require solubilization in the form of a solution, emulsion or dispersion, in aqueous or non-aqueous form. For example, a sunscreen formulation containing aromatic compounds such as Avobenzone (Butyl methoxydibenzoylmethane, Escalol® 517) and/or Oxybenzone (Benzophenone-3, Escalol® 567) as active UVA/UVB absorbing ingredients requires a solubilizing agent to keep them in an emulsion, i.e., to prevent crystallization. Several such solubilizers are known, e.g., $C_{12-15}$ alkyl benzoate (Finsolv® TN); however, they are mediocre solubilizing agents and/or have a 'heavy' feel, which is undesirable in modern cosmetic formulations.

H. Gers-Barlag et al. in U.S. Pat. No. 6,770,269 described a solubilizing agent for triazine derivatives which was an ester of an unbranched alkyl carboxylic acid and a mono- or poly-branched aliphatic alcohol, particularly hexyldecyl laurate, which was derived from lauric acid and hexyldecyl alcohol. Previously, the same authors in U.S. Pat. No. 6,703,001 had described a solubilizing agent for triazine derivatives which was an ester of a branched-chain carboxylic acid and a branched-chain alcohol, particularly isodecyl neopentanoate, which was derived from neopentanoic acid and isodecyl alcohol.

I. Walele et al. in U.S. Pat. No. 6,635,775 described a process for "reduced odor esters" which improved the preparation of established cosmetic esters such as $C_{12-15}$ alkyl benzoates and cetearyl octanoate.

We have previously disclosed in U.S. patent application Ser. No. 11/007,744 that esters of aryl carboxylic acids and aryl alcohols, particularly phenethyl benzoate, which was derived from benzoic acid and 2-phenylethanol, are superior solvents for actives such as sunscreens or UV filters. It was nevertheless surprising, and it could not have been predicted by someone skilled in the art, that combinations of actives with esters of alkyl (including cycloalkyl) carboxylic acids and aryl alcohols would likewise be superior solvents. Completely unprecedented was the discovery that the cyclopropyl group, e.g., in 2-phenylethyl cyclopropanoate; which was derived from cyclopropanecarboxylic acid and 2-phenylethanol, imparts remarkable solubilizing power for the triazines, e.g., Ethylhexyl triazone and Bis-ethylhexyloxyphenol methoxyphenyl triazine.

Accordingly, it is an object of this invention to provide a composition including an active or functional organic compound which is solubilized by a safe and effective organic ester or carbonate as solvent, cosolvent or additive.

Another object is to provide a personal care composition, e.g., a sunscreen or cosmetic composition, or a pharmaceutical, agricultural or industrial composition, containing a solid active or functional organic compound, which is effectively solubilized by an ester of an aryl alcohol, e.g., phenethyl, benzyl or substituted benzyl alcohol, and an alkyl or cycloalkyl carboxylic acid, or a carbonate of an aryl alcohol and an alkyl or cycloalkyl carbonic acid.

A specific object herein is to provide a sunscreen composition containing active UVA and/or UVB compounds which are effectively solubilized by the esters or carbonates of the invention.

These and other objects and features of the invention will be made apparent from the following description.

SUMMARY OF THE INVENTION

What is described herein are effective solubilizing agents for active or functional organic compounds, most particularly, esters of an aryl alcohol, e.g., phenethyl, benzyl or substituted benzyl alcohol, and an alkyl (linear or branched) or cycloalkyl carboxylic acid, or carbonates of said aryl alcohol and an alkyl or cycloalkyl carbonic acid. Preferred esters of the invention are 2-phenylethyl cyclopropanoate, 2-phenylethyl pentanoate and 2-phenylethyl cyclohexanoate, which are new solubilizers for UVA and/or UVB sunscreens or filters.

DETAILED DESCRIPTION OF THE INVENTION

General formulas for the solubilizers of the invention are the following 1a and 1b:

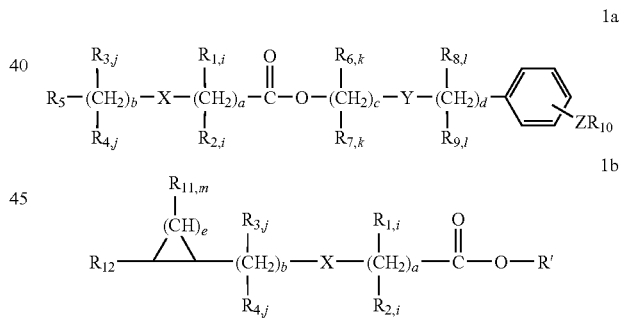

where $R_1$-$R_{12}$ are independently H or branched or unbranched $C_1$-$C_{22}$ alkyl, $C_1$-$C_{22}$ alkoxy, or hydroxy groups; a-e=0-8; and i=0-a, j=0-b, k=0-c, l=0-d and m=0-e; X and Y are independently a heteroatom or $CH_2$, and Z is a heteroatom, H, or $CH_2$; R' in 1b represents the alcohol-derived moiety in 1a. While not explicitly shown in 1b, we include bicyclo and tricyclo compounds. When a=0, carbonates are included for X=O. Other heteroatoms such as X,Y=N or S may be present, and H, O or branched or unbranched $C_1$-$C_{22}$ alkyl groups may also be attached said heteroatoms. Consistent with the rules of structural organic chemistry, only one hydroxy group per C is allowed.

Accordingly, representative solubilizers of the invention are shown in Chart 1 and include 2-phenylethyl cyclopropanoate, 2-phenylethyl pentanoate and 2-phenylethyl cyclohexanoate.

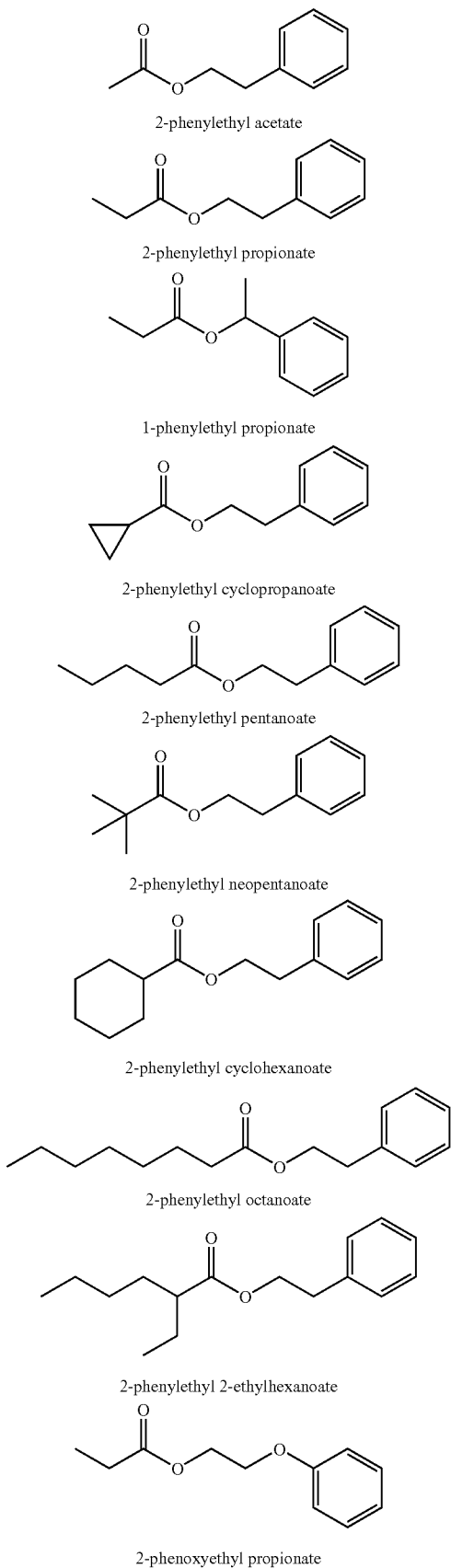

2-phenylethyl acetate 2-phenylethyl propionate 1-phenylethyl propionate 2-phenylethyl cyclopropanoate 2-phenylethyl pentanoate 2-phenylethyl neopentanoate 2-phenylethyl cyclohexanoate 2-phenylethyl octanoate 2-phenylethyl 2-ethylhexanoate 2-phenoxyethyl propionate -continued

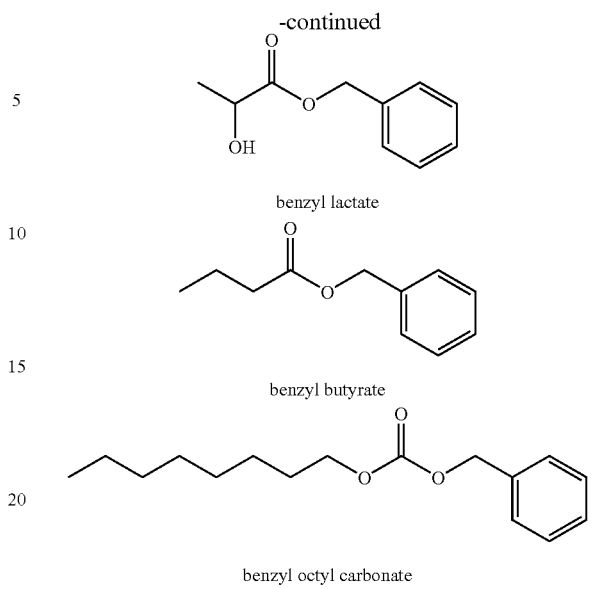

benzyl lactate benzyl butyrate benzyl octyl carbonate

Chart 1. Representative solubilizers of the invention.

Generally, the amount of the solubilizer of the invention in the total weight of the composition is about 1-35 wt. %, preferably 2-20 wt. %.

The active or functional compound in the composition is usually about 0.1-10 wt. % of the composition.

Invention Compositions

Formulations such as sunscreen compositions containing active UVA and UVB compounds, e.g., Avobenzone (E-517), Oxybenzone (E-567), 4-Methylbenzylidene camphor (MBC) Ethylhexyl triazone (EHT), and Bis-ethylhexyloxyphenol methoxyphenyl triazine (BEMT), were effectively solubilized by 2-phenylethyl cyclopropanoate or the other compounds of the invention. Increased critical wavelength and/or boosting of the SPF and/or enhancement of the UVA component of the absorption spectrum relative to the UVB portion were typically observed.

Other UV filter actives that may be employed in the present inventive compositions (and solubilized in 2-phenylethyl cyclopropanoate, 2-phenethyl pentanoate, 2-phenylethyl cyclohexanoate, etc.) include but are not limited to p-Aminobenzoic acid (PABA), Camphor benzalkonium methosulfate, Homosalate, Phenylbenzimidazole sulfonic acid, Terephthalidene dicamphor sulfonic acid, Benzylidene camphor sulfonic acid, Octocrylene, Polyacrylamidomethyl benzylidene camphor, Ethylhexyl methoxycinnamate, PEG-25 PABA, Isoamyl p-methoxycinnamate, Drometrizole trisiloxane, Diethylhexyl butamido triazone, 3-Benzylidene camphor, Ethylhexyl salicylate, Ethylhexyl dimethyl PABA, Benzophenone-4, Benzophenone-5, Methylene bis-benztriazolyl tetramethylbutylphenol, Disodium phenyl dibenzimidazole tetrasulfonate, and Polysilicone-15. Such compositions may include one or more of the aforementioned UV filter actives, including Avobenzone, Oxybenzone, 4-Methylbenzylidene camphor, Ethylhexyl triazone and Bis-ethylhexyloxyphenol methoxyphenyl triazine.

Other actives such as personal care, cosmetic, pharmaceutical, agricultural and industrial compounds are effectively solubilized by the compounds of the invention, including such actives as antibacterial and herbicidal (e.g., algaecidal) compounds, particularly to keep the active in emulsion form without crystallizing or precipitating out of the emulsion, and without requiring the use of large amounts of solvent. Examples of such pharmaceutical compositions include but are not limited to one or more of Furosemide, Lovastatin, Clarithromycin, Diclofenac, Famotidine, Carbamaxepine, Dipridamole, Chlorthiazide, Spironolactone, Dilantin, Imipranine, Melfloquine, Cyclosporine, Glyburide, and Nimodipine. Compositions of the present invention may also include combinations of active or functional organic compounds such as, for example, a pharmaceutical (one or more thereof) and a UV filter active (one or more thereof), as well.

The invention will now be illustrated more particularly by the examples which follow:

EXAMPLE 1

Preparation of 2-Phenylethyl Cyclopropanecarboxylate (2-Phenylethyl Cyclopropanoate)

A 1-L, 4-neck, round-bottom flask, fitted with a thermometer, mechanical stirrer, nitrogen inlet tube and Liebig condenser/receiving flask, was charged with 258.3 g (3.00 mol, 1.00 equiv) of cyclopropanecarboxylic acid, 366.5 g (3.00 mol, 1.00 equiv) of 2-phenylethanol, and 1.14 g (0.2 wt. %) of tin oxalate (Fascat® 2001). The air was removed with three cycles of evacuation/nitrogen-fill using a mechanical vacuum pump (50-100 torr). The rate of stirring was set at ca. 200 rpm, the nitrogen sparge was set at 0.05 scfh, and the reaction mixture was heated to 175° C. After a 2-h hold, 78.0 g of distillate had been collected. The temperature was increased to 180° C. and held for 1 h; an additional 9.6 g of distillate was collected. Finally, the temperature was increased to 190° C. and held for 2 h, and an additional 8.6 g of distillate was collected. The acid number was 5.30 mg KOH/g (98.3% conversion). The excess 2-phenylethanol (12.4% by GLC) and cyclopropanecarboxylic acid (0.82% by GLC) were removed by vacuum distillation through a 15-cm Vigreux column at 95-135° C. (10 torr) in a 101-g forecut. The crude product was distilled at 136-139° C. (10 torr) through a 15-cm Vigreux column to afford 410 g (72%) of 2-phenylethyl cyclopropanecarboxylate (99.1% pure by GLC): residual alcohol, 0.6% (GLC); APHA color, 4.0; acid number, 0.14 mg KOH/g; saponification number, 291 mg KOH/g (theor. 295 mg KOH/g). The cyclopropanecarboxylic acid distilled out of the reaction mixture with the water of reaction can be recycled to improve the yield.

EXAMPLE 2

Preparation of 2-Phenylethyl Pentanoate

A 2-L, 4-neck, round-bottom flask, fitted with a thermometer, mechanical stirrer, nitrogen inlet tube and Liebig condenser/receiving flask, was charged with 612.8 g (6.00 mol, 1.00 equiv) of pentanoic acid, 733.0 g (6.00 mol, 1.00 equiv) of 2-phenylethanol, and 2.50 g (0.2 wt. %) of tin oxalate (Fascat® 2001). The air was removed with three cycles of evacuation/nitrogen-fill using a mechanical vacuum pump (50-100 torr). The rate of stirring was set at ca. 200 rpm, the nitrogen sparge was set at 0.1 scfh, and the reaction mixture was heated to 170° C. After a 1-h hold, 159.3 g of distillate had been collected. It was not possible to get a clean separation; therefore, the organic layer was not returned to the reaction mixture. The temperature was increased to 180, 190, 200 and 210° C. and held for 1 h at each; the amounts of distillate were 21.4, 9.8, 4.9 and 2.2 g, respectively. The acid number was 2.88 mg KOH/g (99.0% conversion). The excess 2-phenylethanol (6.3% by GLC) was removed by vacuum distillation through a 15-cm Vigreux column at 140-165° C. (15-20 torr). The crude product was distilled at 150-155° C. (10 torr, 0.5 scfh nitrogen sweep) to afford 925 g (75%) of 2-phenylethyl pentanoate (99.3% pure by GLC): residual alcohol, 0.3% (GLC); APHA color, 13; acid number, 0.06 mg KOH/g; saponification number, 271 mg KOH/g (theor. 272 mg KOH/g).

EXAMPLE 3

Preparation of 2-Phenylethyl Cyclohexanecarboxylate (2-Phenylethyl Cyclohexanoate)

A 1-L, 4-neck, round-bottom flask, fitted with a thermometer, mechanical stirrer, nitrogen inlet tube and Liebig condenser/receiving flask, was charged with 320.4 g (2.50 mol, 1.00 equiv) of cyclohexanecarboxylic acid, 335.9 g (2.75 mol, 1.10 equiv) of 2-phenylethanol, and 1.20 g (0.2 wt. %) of tin oxalate (Fascat® 2001). The system was heated gently with slow stirring (<50 rpm) until all the cyclohexanecarboxylic acid was in solution. The air was removed with three cycles of evacuation/nitrogen-fill using a mechanical vacuum pump (50-100 torr). The rate of stirring was increased to ca. 200 rpm, the nitrogen sparge was set at 0.1 scfh, and the reaction mixture was heated to 180° C. After a 1-h hold, 36.7 g of distillate had been collected. The alcohol (9.6 g) was separated and returned to the reaction mixture. The temperature was increased to 190° C. and held for 1 h; an additional 14.0 g of distillate was collected. The alcohol (2.5 g) was separated and returned. The temperature was increased to 200° C. and held for 1 h; an additional 4.9 g of distillate was collected. The alcohol (1.0 g) was separated and returned. The temperature was increased to 210° C. and held for 1 h, and an additional 2.1 g of distillate was collected; 0.3 g of alcohol was separated, but not returned. The temperature was increased to 220° C. and held for 2 h, and an additional 1.3 g of distillate was collected; 0.4 g of alcohol was separated, but not returned. The reaction mixture was cooled to room temperature and sampled for analysis. The acid number was 1.04 mg KOH/g (99.5% conversion). Triisodecylphosphite (0.58 g) was added to the reaction mixture, and the excess 2-phenylethanol (3.9% by GLC) was removed by vacuum distillation at 165-170° C. (10 torr, 0.5 scfh nitrogen sweep) for 1 h. Activated carbon (17.4 g, 3 wt. %) was added, and the mixture was heated at 75-80° C. under vacuum (80 torr, 0.5 scfh nitrogen sweep) for 1 h. The product was cooled to room temperature and filtered through Celite® to afford 470 g (81%) of 2-phenylethyl cyclohexanecarboxylate (99.5% pure by GLC): residual alcohol, 0.06% (GLC); APHA color, 89; acid number, 0.21 mg KOH/g; saponification number, 237 mg KOH/g (theor. 241 mg KOH/g).

EXAMPLE 4

Solubility of Solid Organic Sunscreens in Solubilizers of the Invention

Solutions (wt. %) of Avobenzone (E-517), Oxybenzone (E-567), 4-Methylbenzylidene camphor (MBC), Ethylhexyl triazone (EHT) or Bis-ethylhexyloxyphenol methoxyphenyl triazine (BEMT) in each of the solubilizers were prepared at 40-60° C. such that the total mass was 10.00 g. Upon cooling to 25° C., a few seed crystals (<10 mg) of the sunscreen were added to hasten equilibration. The solutions were stored in the dark in a constant temperature chamber at 25° C. Each was sampled weekly, and the ca. 0.1 g sample was filtered through a 0.45μ syringe filter and analyzed by GLC or HPLC, calibrated using standard solutions, until the value for wt. % of solute was constant.

As shown below in Table 1, the solubilizer of the invention is effective in solubilizing at least 10 wt. %, preferably 20 wt. %, most preferably 30 wt. % or more of at least one of the sunscreens. In every case, the solubility of one or more of the sunscreens is significantly higher in the solvent of the invention than the industry standard for the class in question (e.g., esters) or prior art. For example, benzyl lactate is significantly better than $C_{12-15}$ alkyl benzoate (Finsolv® TN) for Oxybenzone (30 vs. 17%). Many of the esters are better across the board, e.g., 2-phenylethyl cyclopropanoate, 2-phenylethyl pentanoate and 2-phenylethyl cyclohexanoate.

Triazines such as EHT and BEMT are particularly challenging to dissolve, and we have discovered a number of solvents that are significantly more effective than the industry standard or prior art, e.g., 2-phenylethyl cyclopropanoate dissolved 16 wt. % of EHT vs. 3 wt. % for isodecyl neopentanoate and 6% for $C_{12}$-15 alkyl benzoate. 2-Phenylethyl propionate (33 wt. %), 2-phenylethyl cyclohexanoate (32 wt. %) and benzyl butyrate (32 wt. %) are at least twice as effective as $C_{12-15}$ alkyl benzoate (16 wt. %) for dissolving BEMT.

Benzyl octyl carbonate is a significantly better solvent than dioctyl carbonate (Cetiol® CC) for Avobenzone, Oxybenzone, 4-Methylbenzylidene camphor, and Bis-ethylhexyloxyphenol methoxyphenyl triazine. The solubilities of Ethylhexyl triazone (6 vs. 7 wt. %, respectively) are the same to within experimental uncertainty (±1%). The differences are especially noteworthy for Oxybenzone (27 vs. 16 wt. %) and BEMT (18 vs. 10 wt. %).

TABLE 1

Solubility data (25° C.) for sunscreen compounds in typical solubilizers of the invention.

| Solvent | Solubility (wt. %) | | | | |
|---|---|---|---|---|---|
| | E-517 | E-567 | MBC | EHT | BEMT |
| 2-phenylethyl acetate | 26 | 44 | 44 | 14 | 26 |
| 2-phenylethyl propionate | 25 | 40 | 44 | 12 | 33 |
| 1-phenylethyl propionate | 23 | 38 | 44 | 10 | 26 |
| 2-phenylethyl cyclopropanoate | 24 | 39 | 42 | 16 | 27 |
| 2-phenylethyl pentanoate | 22 | 35 | 41 | 10 | 27 |
| 2-phenylethyl neopentanoate | 19 | 29 | 38 | 5 | 28 |
| 2-phenylethyl cyclohexanoate | 20 | 32 | 37 | 10 | 32 |
| 2-phenylethyl octanoate | 19 | 27 | 36 | 8 | 23 |
| 2-phenylethyl 2-ethylhexanoate | 17 | 25 | 34 | 4 | 18 |
| 2-phenoxyethyl propionate | 21 | 38 | 39 | 6 | 13 |
| benzyl lactate | 11 | 30 | 30 | 8 | 2 |
| benzyl butyrate | 24 | 39 | 44 | 10 | 32 |
| benzyl octyl carbonate | 17 | 27 | 35 | 6 | 18 |
| isodecyl neopentanoate | 8 | 11 | 26 | 3 | 5 |
| $C_{12-15}$ alkyl benzoate | 15 | 17 | 28 | 6 | 16 |
| dioctyl carbonate | 13 | 16 | 29 | 7 | 10 |

EXAMPLE 5

Enhancement of UVA Absorption

Solutions containing 10 mg/L of sunscreen in selected solvents were prepared, and their UV spectra were measured using a Cary 1E UV-Visible spectrophotometer. The results in Table 2 show that the molar extinction coefficients ε are higher in 2-phenylethyl pentanoate than in $C_{12-15}$ alkyl benzoate for all five sunscreens. They are also higher in 2-phenylethyl cyclohexanoate for Escalol® 517 and Escalol® 567. Generally speaking, greater UVA protection is afforded by the composition with the higher extinction coefficient.

TABLE 2

UV Absorption Data, $\lambda_{max}$ (ε).

| | $\lambda_{max}$ (ε) | | | | |
|---|---|---|---|---|---|
| Solvent | E-517 | E-567 | MBC | EHT | BEMT |
| $C_{12-15}$ alkyl benzoate | 358 (33,400) | 328 (9,260) | N/A (N/A) | N/A (N/A) | 347 (43,800) |
| | N/A (N/A) | 298 (9,310) | 301 (22,000) | 313 (117,000) | 313 (40,800) |
| 2-phenylethyl pentanoate | 359 (34,100) | 327 (9,600) | N/A (N/A) | N/A (N/A) | 345 (48,000) |
| | N/A (N/A) | 287 (14,300) | 298 (23,600) | 312 (123,000) | 312 (42,900) |
| 2-phenylethyl cyclohexanoate | 359 (34,500) | 326 (12,100) | N/A (N/A) | N/A (N/A) | 345 (49,000) |
| | N/A (N/A) | N/A (N/A) | 317 (10,400) | 317 (47,300) | N/A (N/A) |

EXAMPLE 6

Broad Spectrum UVA/UVB Sunscreen Formulations

The 'anti-aging' formulations in Table 3 were examined for critical wavelength, a measure of UVA protection, using an Optometrics SPF 290 analyzer, shortly after preparation and after five freeze-thaw cycles or 1 month of storage at 45° C. The higher the critical wavelength, the greater the UVA protection. As can be seen in Table 4, the formulation containing 2-phenylethyl cyclohexanoate was superior to the other formulations containing Finsolv® TN, Eldew® SL-205, Finsolv® TPP, or Elefac® I-205.

TABLE 3

Anti-aging cream formulations.

| | Formulation | | | | |
|---|---|---|---|---|---|
| Ingredient | 1 Wt. % | 2 Wt. % | 3 Wt. % | 4 Wt. % | 5 Wt. % |
| Phase A | | | | | |
| Deionized water | 57.35 | 57.35 | 57.35 | 57.35 | 57.35 |
| Stabileze ® QM | 0.50 | 0.50 | 0.50 | 0.50 | 0.50 |
| Butylene glycol | 3.00 | 3.00 | 3.00 | 3.00 | 3.00 |
| Disodium EDTA | 0.10 | 0.10 | 0.10 | 0.10 | 0.10 |
| Phase B | | | | | |
| Cerasynt ® 840 | 1.50 | 1.50 | 1.50 | 1.50 | 1.50 |
| Cerasynt ® 945 | 2.00 | 2.00 | 2.00 | 2.00 | 2.00 |
| Escalol ® 517 | 3.00 | 3.00 | 3.00 | 3.00 | 3.00 |
| Escalol ® 557 | 7.50 | 7.50 | 7.50 | 7.50 | 7.50 |
| Escalol ® 567 | 2.00 | 2.00 | 2.00 | 2.00 | 2.00 |
| Escalol ® 587 | 5.00 | 5.00 | 5.00 | 5.00 | 5.00 |
| Phenethyl cyclohexanoate | 10.00 | 0.00 | 0.00 | 0.00 | 0.00 |
| Finsolv ® TN | 0.00 | 10.00 | 0.00 | 0.00 | 0.00 |
| Eldew ® SL-205 | 0.00 | 0.00 | 10.00 | 0.00 | 0.00 |
| Finsolv ® TPP | 0.00 | 0.00 | 0.00 | 10.00 | 0.00 |
| Elefac ® I-205 | 0.00 | 0.00 | 0.00 | 0.00 | 10.00 |
| Phase C | | | | | |
| Sodium hydroxide, 10 wt. % | 1.30 | 1.30 | 1.30 | 1.30 | 1.30 |
| Deionized water | 5.00 | 5.00 | 5.00 | 5.00 | 5.00 |

TABLE 3-continued

Anti-aging cream formulations.

| | Formulation | | | | |
|---|---|---|---|---|---|
| Ingredient | 1 Wt. % | 2 Wt. % | 3 Wt. % | 4 Wt. % | 5 Wt. % |
| Phase D | | | | | |
| Liquapar ® Optima | 1.25 | 1.25 | 1.25 | 1.25 | 1.25 |
| Liquapar ® Oil | 0.40 | 0.40 | 0.40 | 0.40 | 0.40 |
| Phase E | | | | | |
| Glycacil ®-L | 0.10 | 0.10 | 0.10 | 0.10 | 0.10 |
| | 100.00 | 100.00 | 100.00 | 100.00 | 100.00 |

Typical Preparation: For Phase A, a beaker was charged with water, butylene glycol and disodium EDTA. Mixing was begun, and Stabileze® QM was slowly sifted into it. The batch was heated to 80° C. with mixing and held for 45 min. In a separate beaker, the ingredients for Phase B were combined, mixed and heated to 75° C. Phase C was slowly added to Phase A, and the batch was mixed until clarity was obtained. Phase B was added, and the batch was cooled to 45° C. with mixing. Phase D was added and mixed thoroughly. Phase E was added and mixed thoroughly. After qs for water loss, the batch was packaged.

TABLE 4

Critical wavelength data.

| | Critical wavelength (nm) | | |
|---|---|---|---|
| Formulation | initial | freeze-thaw | 45° C.-storage |
| 1 | 377.6 | 377.7 | 376.8 |
| 2 | 375.0 | 374.7 | 373.3 |
| 3 | 375.0 | 374.3 | 374.1 |
| 4 | 374.8 | 373.9 | 373.8 |
| 5 | 373.1 | 373.7 | 372.5 |

While the invention has been described with particular reference to certain embodiments thereof, it will be understood that changes and modifications may be made which are within the skill of the art. Accordingly, it is intended to be bound only by the following claims.

What is claimed is:

1. A composition of an active or functional organic compound solubilized in 2-phenylethyl cyclopropanoate.

2. A composition according to claim 1 in which said active compound is a solid organic compound.

3. A composition according to claim 1 wherein said active or functional compound is a personal care, cosmetic, or pharmaceutical compound.

4. A composition according to claim 1 which is a sunscreen composition.

5. A sunscreen composition according to claim 4 in which said active compound is solubilized in an amount of at least 10 wt. %.

6. A sunscreen composition according to claim 4 in which said active is avobenzone, oxybenzone, 4-methylbenzylidene camphor, ethylhexyl triazone or bis-thylhexyloxyphenol methoxyphenyl triazine, or mixtures thereof.

7. A sunscreen composition according to claim 5 in which said active is avobenzone, oxybenzone, 4-methylbenzylidene camphor, ethylhexyl triazone or bis-ethylhexyloxyphenol methoxyphenyl triazine, or mixtures thereof.

8. A sunscreen composition according to claim 4 in which said active is selected from the group consisting of avobenzone, benzophenone-3, benzophenone-4, benzophenone-5, 4-methylbenzylidene camphor, p-aminobenzoic acid (PABA), camphor benzalkonium methosulfate, homosalate, phenylbenzimidazole sulfonic acid, terephthalidene dicamphor sulfonic acid, benzylidene camphor sulfonic acid, octocrylene, polyacrylamidomethyl benzylidene camphor, ethylhexyl methoxycinnamate, PEG-25 PABA, isoamyl p-methoxycinnamate, ethylhexyl triazone, drometrizole trisiloxane, diethylhexyl butamido triazone, 3-benzylidene camphor, ethylhexyl salicylate, ethylhexyl dimethyl PABA, methylene bis-benztriazolyl tetramethylbutylphenol, disodium phenyl dibenzimidazole tetrasulfonate, bis-ethylhexyloxyphenol methoxyphenyl triazine, polysilicone-15, and mixtures thereof.

9. A sunscreen composition according to claim 5 in which said active is selected from the group consisting of avobenzone, benzophenone-3, benzophenone-4, benzophenone-5, 4-methylbenzylidene camphor, p-aminobenzoic acid (PABA), camphor benzalkonium methosulfate, homosalate, phenylbenzimidazole sulfonic acid, terephthalidene dicamphor sulfonic acid, benzylidene camphor sulfonic acid, octocrylene, polyacrylamidomethyl benzylidene camphor, ethylhexyl methoxycinnamate, PEG-25 PABA, isoamyl p-methoxycinnamate, ethylhexyl triazone, drometrizole trisiloxane, diethylhexyl butamido triazone, 3-benzylidene camphor; ethylhexyl salicylate; ethylhexyl-dimethyl PABA; methylene bis-benztriazolyl tetramethylbutylphenol, disodium phenyl dibenzimidazole tetrasulfonate, bis-ethylhexyloxyphenol methoxyphenyl triazine, polysilicone-15, and mixtures thereof.

10. A composition according to claim 1 wherein said active or functional organic compound is selected from the group consisting of agricultural and industrial compounds.

11. A composition according to claim 1 wherein said active or functional organic compound is selected from the group consisting of furosemide, lovastatin, clarithromycin, diclofenac, famotidine, carbamaxepine, dipyridamole, chlorthiazide, spironolactone, dilantin, imipranine, mefloquine, cyclosporine, glyburide, nimodipine, and mixtures thereof.

12. A composition according to claim 1 comprising a UV filter compound and a pharmaceutical compound.

13. A composition according to claim 1 comprising at least two active or functional organic compounds selected from the group consisting of UV filter, cosmetic, and pharmaceutical compounds.

14. A composition according to claim 12 comprising a UV filter compound selected from the group consisting of avobenzone, benzophenone-3, benzophenone-4, benzophenone-5, 4-methylbenzylidene camphor, p-aminobenzoic acid (PABA), camphor benzalkonium methosulfate, homosalate, phenylbenzimidazole sulfonic acid, terephthalidene dicamphor sulfonic acid, benzylidene camphor sulfonic acid, octocrylene, polyacrylamidomethyl benzylidene camphor, ethylhexyl methoxycinnamate, PEG-25 PABA, isoamyl p-methoxycinnamate, ethylhexyl triazone, drometrizole trisiloxane, diethylhexyl butamido triazone, 3-benzylidene camphor, ethylhexyl salicylate, ethylhexyl dimethyl PABA, methylene bis-benztriazolyl tetramethylbutylphenol, disodium phenyl dibenzimidazole tetrasulfonate, bis-ethylhexyloxyphenol methoxyphenyl triazine, polysilicone-15, and mixtures thereof, and a pharmaceutical compound selected from the group consisting of furosemide, lovastatin, clarithromycin, diclofenac, famotidine, carbamaxepine, dipyridamole, chlorthiazide, spironolactone, dilantin, imipranine, melfloquine, cyclosporine, glyburide, nimodipine, and mixtures thereof.

* * * * *